United States Patent [19]
Dietz et al.

[11] Patent Number: 5,510,494
[45] Date of Patent: Apr. 23, 1996

[54] PROCESS FOR THE PREPARATION OF $C_1$–$C_4$-ALKYL OR $C_1$–$C_4$-ALKOXY AND UNSUBSTITUTED 2-(CYANOMETHYL)BENZIMIDAZOLE

[75] Inventors: Erwin Dietz, Kelkheim/Ts.; Gustav Kapaun, Bad Soden, both of Germany

[73] Assignee: Hoechst AG, Germany

[21] Appl. No.: 200,743

[22] Filed: Feb. 23, 1994

[30] Foreign Application Priority Data

Feb. 25, 1993 [DE] Germany ............. 43 05 714.4

[51] Int. Cl.⁶ ............................................. C07D 235/14
[52] U.S. Cl. ........................................................ 548/309.7
[58] Field of Search ............................................ 548/309.7

[56] References Cited

FOREIGN PATENT DOCUMENTS 1361778  4/1964  France.
2900506  7/1980  Germany.
154773  12/1984  Ind..

OTHER PUBLICATIONS

Copeland, R. "The Preparation and Reactions of 2–Benzimidazolecarboxylic Acid and 2–Benzimidazoleacetic Acid" J. Am. Chem. Soc., 1943, (65), pp. 1072–1075.

Sawlewicz, J., et al, *Pol. J. Pharmacol. Pharm.* 26: 642 (1974).

*Primary Examiner*—Jacqueline Haley
*Attorney, Agent, or Firm*—Connolly & Hutz

[57] ABSTRACT

Process for the preparation of substituted and unsubstituted 2-(cyanomethyl)benzimidazole A process for the preparation of substituted or unsubstituted 2-(cyanomethyl)benzimidazole, of the formula (I)

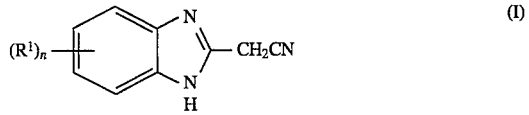

which comprises reacting an o-phenylenediamine of the formula (II)

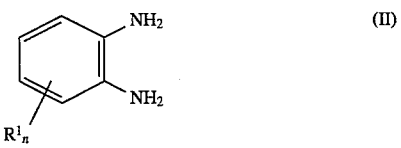

in which $R^1$ is $C_1$–$C_4$-alkyl or $C_1$–$C_4$-alkoxy, preferably methyl or methoxy, and n is an integer from 0 to 2, preferably 0 or 1, in particular 0, with a cyanoacetic ester of the formula (III)

$$NC-CH_2-COOR^2 \qquad (III)$$

in which $R^2$ is unsubstituted or substituted, linear, branched or cyclic $C_2$–$C_{12}$-alkyl and 1 to 3 $CH_2$ groups of the alkyl radical can in each case be replaced by oxygen, at a temperature of 150°–175° C. in a halogen-free inert solvent whose boiling point is 150° C. or more, or in a mixture of two or more of such solvents, without adding an aromatic sulfonic acid as catalyst.

Using the process according to the invention, 2-(cyanomethyl)benzimidazoles are prepared without a catalyst in good yields and high purity.

10 Claims, No Drawings

PROCESS FOR THE PREPARATION OF $C_1$-$C_4$-ALKYL OR $C_1$-$C_4$ – ALKOXY AND UNSUBSTITUTED 2-(CYANOMETHYL)BENZIMIDAZOLE 2-(Cyanomethyl)benzimidazole is a known compound. Its preparation is described, for example, in DE-A-2,900,506, in the Indian Patent 154,773, in FR-A-1,361,778 and in Sawlewicz, J. and Milczarska, B., Pol. J. Pharmacol. Pharm. 26, (1974), p. 642, the two last-mentioned references also describing the preparation of substituted 2-(cyanomethyl)benzimidazoles.

In the abovementioned publications, the preparation of 2-(cyanomethyl)benzimidazole follows the equation below:

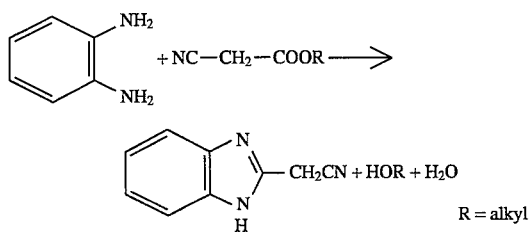

R = alkyl

In DE-A-2,900,506, this condensation is carried out without using a solvent. The disadvantages are that impure products and only low yields are obtained.

In FR-A-1,361,778 and in the Indian Patent 154,773, halogenated aromatics, especially o-dichlorobenzene, are employed as solvents.

Moreover, the use of an acidic catalyst is described, preferably an aromatic sulfonic acid.

In Sawlewicz, J. and Milczarska, B., Pol. J. Pharmacol. Pharm. 26, (1974), p. 642, 2-(cyanomethyl)benzimidazole is prepared in anhydrous xylene under reflux without a catalyst. However, the yield is only 67%..

It is the object of the present invention to provide a process for the preparation of $C_1$-$C_4$ alkoxyl or $C_1$-$C_4$ alkoxy and unsubstituted 2-(cyanomethyl)benzimidazole, which overcomes the disadvantages of halogenated solvents, low yields and impure products.

It has been found that 2-(cyanomethyl)benzimidazole and derivatives thereof can, surprisingly, be prepared in good yields and high purity, even without the use of a catalyst, by carrying out the condensation reaction at a temperature in the range from 150° to 175° C. in a halogen-free inert solvent whose boiling point is 150° C. or more, or in a mixture of such solvents.

The invention relates to a process for the preparation of $C_1$-$C_4$ alkyl or $C_1$-$C_4$ alkoxy or unsubstituted 2-(cyanomethyl)benzimidazole, of the formula (I)

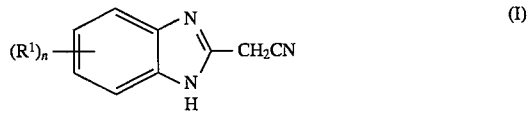

which comprises reacting an o-phenylenediemine of the formula (II)

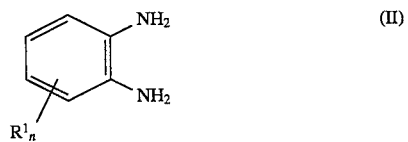

in which $R^1$ is $C_1$-$C_4$-alkyl or $C_1$-$C_4$-alkoxy, preferably methyl or methoxy, and n is an integer from 0 to 2, preferably 0 or 1, in particular 0, with a cyanoacetic ester of the formula (III)

in which $R^2$ is unsubstituted or $C_1$-$C_4$ alkyl or $C_1$-$C_4$ alkoxy, linear, branched or cyclic $C_2$-$C_{12}$-alkyl and 1 to 3 $CH_2$ groups of the alkyl radical can in each case be replaced by oxygen, at a temperature of 150°–175° C. in a halogen-free inert solvent whose boiling point is 150° C. or more, or in a mixture of two or more of such solvents, without adding an aromatic sulfonic acid as catalyst.

o-Phenylenediamines which are of interest are, for example:
  4-methyl-1,2-diaminobenzene, 4-methoxy-1,2-diaminobenzene and 4-ethoxy-1,2-diaminobenzene. Unsubstituted 1,2-diaminobenzene is particularly preferred.

Cyanoacetic esters which are of interest are those in which the radical $R^2$ is ethyl, n-propyl, n-butyl, isobutyl, n- and iso-pentyl, 2-ethylhexyl, n-octyl, 2-methoxyethyl or 2-ethoxyethyl. n-Propyl cyanoacetate, n- and iso-butyl cyanoacetate and n- and iso-pentyl cyanoacetate are preferred, and n-butyl cyanoacetate and iso-butyl cyanoacetate are particularly preferred.

The cyanoacetic esters of the formula (III) can be employed individually or in the form of a mixture. It is advantageous to add at least one more cyanoacetic ester of the formula (III) to the reaction mixture, in particular when ethyl cyanoacetate is used. Even though it is also possible, in principle, to use ethyl cyanoacetate on its own, 2-(cyanomethyl)benzimidazole is obtained in a poorly, crystalline form, which causes problems during work-up. This disadvantage can be overcome by adding other alkyl cyanoacetates, for example n- or iso-butyl cyanoacetate. A mixture of ethyl cyanoacetate with n- or iso-butyl cyanoacetate is therefore particularly preferred.

A mixture of ethyl and n-butyl cyanoacetate can be obtained by transesterifying ethyl cyanoacetate with n-butanol with an addition of conventional transesterification catalysts, for example an aromatic sulfonic acid. It is not necessary to wait until a quantitative transesterification has ended, but the reaction can be stopped during a partial conversion stage. These transesterification catalysts do not have to be separated from the transesterification mixture if this is subjected to a further reaction with o-phenylene diamines according to the process of the invention. They can remain during the subsequent reaction for the preparation of 2-(cyanomethyl)benzimidazoles, but this does not have any advantages.

Even though good results can be obtained with the $C_6$-$C_{12}$-alkyl esters, their higher molecular weight in combination with a lower percentage of active substance

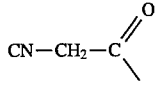

is uneconomical with regard to weight.

Solvents which are suitable for the process according to the invention are all halogen-free, optionally oxygen-containing hydrocarbons which are inert under the reaction conditions with regard to the reactants and whose boiling point is 150° C. or above. The solvents according to the invention can be cycloaliphatic substances, olefins, cycloolefins, alkoxy aromatic substances, araliphatic substances or aromatic substances, preferably an aromatic hydrocarbon fraction whose lower limit of the boiling range is 150° C. or above, furthermore cumene, phenetole, mesitylene, decalin, tattalin, 1,2,3-trimethylbenzene, 1,2,4-trimethylbenzene, n-propylbenzene, 1-methyl-4-propylbenzene, 1-methyl-4-ethylbenzene, 1-methyl-3-ethylbenzene, 1-methyl-2-ethylbenzene, o, m, p-methyl-isopropylbenzene, 1,3-diethylbenzene, 1,4-diethylbenzene, 1-ethyl-3,5-dimethylbenzene, 2-ethyl-1,3-dimethylbenzene, 2-ethyl-1,4-dimethylbenzene, 4-ethyl-1,3-dimethylbenzene, 4-ethyl-1,2-dimethylbenzene, 1-methyl-2-propylbenzene, n-butylbenzene, 1,2,4,5-tetramethylbenzene, 1,2,3,5-tetramethylbenzene, 1,2,3,4-tetramethylbenzene or mixtures of the abovementioned compounds.

Other suitable solvents are mono- and bicyclic monoterpenes with or without oxygen, as they can be obtained in the form of technical-grade products from natural raw materials, such as, for example, from oil of turpentine or by sulfate digestion of wood. [see Ullmann, 4th Edition (1982), Volume 22, Tarpens [Tarpenes], p. 535 et seq. and Terpentinöl [Oil of turpentine], p. 553 et seq.]. These products are mixtures of various individual components which are essentially monoterpenes. Suitable monocyclic monoterpenes are, for example, the classes of the p-menthadienes, such as α-terpinene and dipentene, and the bicyclic monoterpenes, such as 3-carene and α-pinene. Suitable oxygen-containing monoterpenes are, for example, α-terpineol and cineol. All these solvents can be recycled in an ecologically advantageous manner.

The reaction is carried out in a temperature range from 150° to 175° C., preferably 160° to 170° C. While noticeably longer reaction times are required at the lower temperature limit, the upper temperature limit already involves the danger of considerable amounts of by-products being formed. A temperature range from 155° to 170° C. is therefore particularly preferred. Depending on the cyanoacetic ester and solvent employed, the abovementioned condensation reaction has a narrow temperature optimum, which must be determined by experiments in each individual case.

The stoichiometric ratios of the o-phenylenediamine and the cyanoacetic ester employed are preferably 1:1.0 to 1:1.1, in particular 1:1.04 to 1:1.06. An excess of o-phenylenediamine is not expedient. The yield is not improved, and the excess o-phenylenediamine contaminates the solvent. A small excess of 4 to 6 mol % of the cyanoacetic ester gives the best yields, while a larger excess is disadvantageous since it does not increase the yield and by-products which are formed contaminate the desired product.

The reaction time is expediently 5 to 30 hours. Alcohol and water which are eliminated are distilled off during the reaction.

Using the process according to the invention, the desired products are obtained in good purity and in crystalline form so that, as a rule, they can be processed without further purification. Moreover, ecologically unfavorable halobenzenes, such as o-dichlorobenzene, can be dispensed with as solvents.

2-(Cyanomethyl)benzimidazole and derivatives thereof are valuable intermediates for the syntheses of colorants, pigments, crop protection agents and pharmaceuticals.

To determine the purity, HPLC analyses were carried out. The samples were dissolved in methanol in an ultrasonic bath to give a clear solution. This solution was filtered through a prefilter. The precolumn and main column were RP columns (reversed phase). The eluent was methanol in a mixture with an 0.5% strength aqueous sodium acetate/glacial acetic acid buffer of pH 7. Calibration was against pure substance. 2-(Cyanomethyl)benzimidazole was detected at 272 nm.

The examples below are intended to illustrate the invention. The parts mentioned are parts by weight, the percentages are by weight, unless otherwise indicated.

EXAMPLE 1

27 parts of 1,2-diaminobenzene and 37 parts of iso-butyl cyanoacetate were heated for 10 hours at 165° C. in 125 parts of an aromatic hydrocarbon fraction of boiling range 185°–211° C. under a stream of nitrogen. Isobutanol and water formed were distilled off during this period. The mixture was allowed to cool to room temperature and subjected to filtration with suction. The solids were washed with 40 parts of the aromatic hydrocarbon fraction. The remaining with solvent was removed from the filter cake at 100° to 120° C. in vacuo.

Yield: 35.4 parts (90.2% of theory) of product in the form of good crystals, m.p. 208°–209° C.

HPLC analysis of the product revealed a content of 94.2% 2-(cyanomethyl)benzimidazole. Accordingly, the yield is 85% of theory based on 100% product.

COMPARATIVE EXAMPLE 1

If the above Example 1 is compared with Example 2 of FR-A-1,361,778, which also employs iso-butyl cyanoacetate, the following comparison, which reveals the superiority of the process according to the invention, results:

|  | Example 1 | Comparative example Example 2 of FR-A-1,361,778 |
| --- | --- | --- |
| Yield [%] | 90.2 | 70 |
| M.p. [°C.] | 208–209 | 201 |
| Purity [%] | 94.2 | No information |

|  | Example 1 | Comparative example Example 2 of FR-A-1,361,778 |
| --- | --- | --- |
| Yield [%] | 85 | <70 |
| Catalyst employed | none | p-toluenesulfonic acid |
| Reaction temp. [°C.] | 165 | 180–190 |
| Solvent | aromatic hydrocarbon | o-dichlorobenzene |

EXAMPLE 2

27 parts of 1,2-dieminobenzene and 29.5 parts of ethyl cyanoacetate were heated for 10 hours at 165° C. in 125 parts of an aromatic hydrocarbon fraction of boiling range 185°–211° C. under a stream of $N_2$. Ethanol and water were distilled off. The mixture was allowed to cool and the product was washed with 40 parts of the aromatic hydrocarbon fraction. The remaining solvent was removed in vacuo at 100°–120° C. The product prepared in this example is in the form of less good crystals than the product prepared in Example 1.

Yield: 36.8 parts of product.

HPLC analysis of the product revealed a 2-(cyanomethyl)-benzimidazole content of 91.4%. Accordingly, the yield is 86% of theory based on 100% product.

COMPARATIVE EXAMPLE 2

If the results of the above Example 2 are compared with Example 3 of Indian Patent 154,773, which also employs ethyl cyanoacetate, the following comparison, which reveals the superiority of the process according to the invention with regard to product purity, yield, solvent used, economy and dispensibility of a catalyst, results:

|  | Example 2 | Example 3 of Indian Patent 154,773 | |
|---|---|---|---|
|  |  | Information | Data obtained by reproduction |
| Yield [%] | 93.8 | 90 | 98 |
| Purity [%] | 91.4 | no information | 77.5 |
| Yield [%] | 85.6 | no information | 76 |
| Catalyst employed | none | p-toluenesulfonic acid | |
| Solvent | aromatic hydrocarbon | o-dichlorobenzene | |
| Reaction temperature | 165° C. | 175° C. | |
| Filtration temperature | 25° C. | 0–5° C. | |

EXAMPLE 3

27 parts of 1,2-diaminobenzene and 37 parts of n-butyl cyanoacetate were refluxed for 24 hours in 125 parts of cumene (b.p. 152° C.) under a stream of nitrogen. Butanol and water were distilled off. The mixture was allowed to cool, and the product was washed with cumene. The remaining solvent was removed in vacuo at 100°–120° C.

Yield: 84% of theory, m.p. 206°–209° C. HPLC analysis revealed a product content of 85.6%. Accordingly, the yield was 72% of theory, based on 100% product. This experiment shows that the yield is already down at the lower temperature limit according to the invention.

COMPARATIVE EXAMPLE 3

If the maximum temperature limit according to the invention of 175° C. is exceeded, for example if the process is carried out at 180° C., a much lower yield is obtained. If the process is carried out as described in Example 4a below and the mixture is heated at 180° C. instead of 167° C., the following data are obtained:

Yield: 42.0 g, m.p. 192°–250° C. (decomposition)

HPLC analysis revealed a product content of 33.8%. Accordingly, the yield was only 36% of theory based on 100% substance.

EXAMPLE 4a 27 parts of 1,2-dimainobenzene and 37 parts of n-butyl cyanoacetate were heated for 10 hours at 167° C. in 125 parts of an aromatic hydrocarbon fraction of boiling range 185°–211° C. under a stream of nitrogen. n-Butanol and water were distilled off. The mixture was allowed to cool and subjected to filtration with suction. The solids were washed with 40 parts of the aromatic hydrocarbon fraction. The remaining solvent was removed in vacuo at 100°–120° C. The product has the form of good crystals.

Yield: 33.8 parts of product, m.p. 208°–210° C. Analysis of the product by means of HPLC revealed a 2-(cyanomethyl)benzimidazole content of 95.1%. Accordingly, the yield was 86% of theory based on 100% product.

EXAMPLE 4b

The experiment of Example 4a was repeated, but the aromatic hydrocarbon fraction used was replaced by a lower boiling aromatic hydrocarbon fraction of boiling range 166°–184° C., and the result obtained was as follows:

Yield: 36.6 parts of product, m.p.: 203°–207°C.

Analysis of the product by means of HPLC revealed a 2-(cyanomethyl)benzimidazole content of 94.2%.

Accordingly, the yield is 87.8% of theory based on 100% product.

EXAMPLES 5 to 10

The procedure of Example 4a was followed, and the cyanoacetic esters mentioned in the table below were employed at the reaction temperatures indicated.

| Ex. | Cyanoacetic ester ($R^2$ =) | Reaction temp. [°C.] | Melting points of the product obtained [°C.] | Purity [%] | Yield (based on 100% product) [%] |
|---|---|---|---|---|---|
| 5 | propyl | 160 | 207–209 | 96.8 | 83 |
| 6 | pentyl | 165 | 209–210 | 99.9 | 85 |
| 7 | 2-ethylhexyl | 167 | 208–211 | 98.5 | 85 |
| 8 | n-octyl | 167 | 208–210 | 99.5 | 80 |
| 9 | 2-methoxyethyl | 160 | 201–207 | 91.6 | 85 |
| 10 | 2-ethoxyethyl | 158 | 208–210 | 99.8 | 86 |

EXAMPLES 11a–c

The procedure of Example 2 was followed, and in a: 75%, in b: 50%, and in c: 25% respectively of the ethyl cyanoacetate was replaced by n-butyl cyanoacetate, and products of good crystallinity having the following melting points were obtained in the following yields:

| Example | M.p. [°C.] | Yield [% of theory] based on 100% product |
|---|---|---|
| 11a | 202–210 | 86 |
| 11b | 204–209 | 87 |
| 11c | 203–208 | 88 |

EXAMPLE 12

27 parts of 1,2-diaminobenzene and 37 parts of n-butyl cyanoacetate were heated for 10 hours at 165°–166° C. in 125 parts of phenetole under a stream of nitrogen. n-Butanol and water were distilled off. The mixture was allowed to cool to room temperature and subjected to filtration with suction. The solids were washed with 40 parts of phenetole. The filter cake was dried in vacuo at 100°– 120° C. A product in the form of good crystals was obtained.

Yield: 34.4 parts, m.p. 205°–210° C. HPLC analysis revealed a product content of 96.7%. Accordingly, the yield was 84.8% of theory based on 100% product.

EXAMPLE 13

The procedure of Example 12 was followed, but a technical-grade mixture of p-menthadienes was used instead of phenetole and the following results were obtained:

Yield: 36.6 parts, m.p. 202°–207° C.

HPLC analysis revealed a product content of 89.6%. Accordingly, the yield was 83.5% of theory based on 100% product.

EXAMPLE 14

5-Methyl-2-(cyanomethyl)benzimidazole 30.5 parts of 3,4-diaminotoluene and 37.0 parts of n-butyl cyanoacetate were heated for 10 hours at 160° C. in 125 parts of an aromatic hydrocarbon fraction of boiling range 185°–211° C. under a stream of nitrogen, and the n-butanol and water which were eliminated were distilled off. The mixture was allowed to cool and subjected to filtration. The solids were washed with 45 parts of the aromatic hydrocarbon fraction. The remaining solvent which adhered to the product was removed in vacuo at 100° C.

Yield: 34 parts of the product, 80% of theory.

M.p.: 186°–187° C.

While the melting point is virtually identical (186°– 188° C.), this process is clearly superior to the process for the preparation of 5-methyl-2-(cyanomethyl)benzimidazole which was described by J. Sawlewicz et al. in Pol. J. Pharmacol. Pharm. 1974, 26, p. 642, in which the yield is 44%.

We claim:

1. A process for the preparation of alkylated or alkoxylated or unsubstituted 2-(cyanomethyl)benzimidazole, of the formula (I)

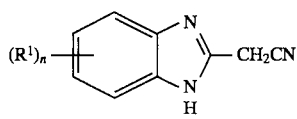

by reacting an o-phenylenediamine of the formula (II)

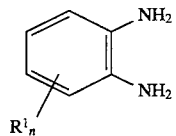

in which $R^1$ is $C_1$–$C_4$-alkyl or $C_1$–$C_4$-alkoxy and n is an integer from 0 to 2, with a cyanoacetic ester of the formula (III)

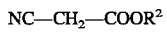

in which $R^2$ is unsubstituted or substituted, linear, branched or cyclic $C_2$–$C_{12}$-alkyl said alkyl optionally substituted by one to three alkoxy groups at a temperature of 150°–175° C. in a halogen-free inert solvent wherein the solvent is an aromatic araliphatic or alkoxyaromatic substance whose boiling point is 150° C. or above or an aromatic hydrocarbon fraction whose lower limit of the boiling range is 150° C. or above or in a mixture of two or more of such solvents, without adding an aromatic sulfonic acid as catalyst.

2. The process as claimed in claim 1, wherein the reaction is carried out at a temperature of 155° to 170° C.

3. The process as claimed in claim 1, wherein n is the number 1.

4. The process as claimed in claim 1, wherein $R^1$ is methyl or methoxy.

5. The process as claimed in claim 1, wherein n is the number 0.

6. The process as claimed in claim 1, wherein $R^2$ is ethyl, n-propyl, n-butyl, iso-butyl, n-pentyl, iso-pentyl, 2-ethylhexyl, n-octyl, 2-methoxyethyl or 2-ethoxyethyl.

7. The process as claimed in claim 1, wherein a mixture of various cyanoacetic esters of the formula (III) is employed.

8. The process as claimed in claim 1, wherein ethyl cyanoacetate is employed in the form of a mixture with n-butyl cyanoacetate or iso-butyl cyanoacetate.

9. The process as claimed in claim 1, wherein the solvent is cumene, mesitylene, phenetole or a mixture thereof.

10. The process as claimed in claim 1, wherein the solvent is a monocyclic or bicyclic monoterpene or a mixture which consists essentially of monoterpenes.

* * * * *

UNITED STATES PATENT AND TRADEMARK OFFICE
CERTIFICATE OF CORRECTION

PATENT NO. : 5,510,494
DATED : April 23, 1996
INVENTOR(S) : Dietz, et al

It is certified that error appears in the above-indentified patent and that said Letters Patent is hereby corrected as shown below:

Col. 1, line 39, "$C_1$-$C_4$-alkoxyl" should read -- $C_1$-$C_4$-alkyl --.

Col. 1, line 58, "o-phenylenediemine" should read -- o-phenylenediamine --.

Col. 2, last line, "tattalin" should read -- tetralin --.

Col. 3, line 11, "monotarpenes" should read -- monoterpenes --.

Col. 3, line 15, "Tarpen[Tarpens]" should read -- Terpene[Terpenes] --.

Col. 3, line 22, "monotarpenes" should read -- monoterpenes --.

Col. 4, line 48, "1,2-dieminobenzene" should read -- 1,2-diaminobenzene --.

Signed and Sealed this

First Day of April, 1997

*Attest:*

BRUCE LEHMAN

*Attesting Officer*  Commissioner of Patents and Trademarks